(12) United States Patent
Dannenberg et al.

(10) Patent No.: US 6,200,760 B1
(45) Date of Patent: *Mar. 13, 2001

(54) METHOD OF SCREENING AGENTS AS CANDIDATES FOR DRUGS OR SOURCES OF DRUGS

(75) Inventors: Andrew J. Dannenberg, New York; Kotha J. Subbaramaiah, Flushing, both of NY (US); David S. Pasco, Oxford, MS (US)

(73) Assignees: Cornell Research Foundation, Inc., Ithaca, NY (US); The University of Mississippi, University, MS (US)

(*) Notice: Subject to any disclaimer, the term of this patent is extended or adjusted under 35 U.S.C. 154(b) by 0 days.

(21) Appl. No.: 09/355,940

(22) PCT Filed: Jan. 12, 1998

(86) PCT No.: PCT/US98/00023

§ 371 Date: Aug. 13, 1999

§ 102(e) Date: Aug. 13, 1999

(87) PCT Pub. No.: WO98/37235

PCT Pub. Date: Aug. 27, 1998

Related U.S. Application Data

(60) Provisional application No. 60/038,254, filed on Feb. 24, 1997.

(51) Int. Cl.[7] ............................... C12Q 1/68; C12Q 1/66; C12P 19/34
(52) U.S. Cl. ............... 435/6; 435/4; 435/8; 435/91.1; 435/471; 435/476
(58) Field of Search .................... 435/6, 4, 91.1, 435/471, 476, 8

(56) References Cited

U.S. PATENT DOCUMENTS

| | | | |
|---|---|---|---|
| 5,445,941 | 8/1995 | Yang | 435/6 |
| 5,457,107 | 10/1995 | Kaufman | 514/236.2 |
| 5,521,213 | 5/1996 | Prasit et al. | 514/443 |
| 5,532,265 | 7/1996 | Gijbels et al. | 514/419 |
| 5,543,297 | * 8/1996 | Cromlish | 435/25 |
| 5,556,754 | 9/1996 | Singer et al. | 435/6 |
| 5,569,558 | 10/1996 | Ashby et al. | 435/6 |
| 5,585,504 | 12/1996 | Desmond et al. | 549/323 |
| 5,824,794 | * 10/1998 | Borden | 536/24.1 |
| 5,837,479 | * 11/1998 | Young et al. | 435/25 |
| 5,877,202 | * 10/1998 | Bitonti | 514/419 |
| 6,048,850 | 4/2000 | Young et al. | 514/183 |

OTHER PUBLICATIONS

Buttice, G., et al., Nucleic Acids Research, 19, 3723–3731 (1991).

Kosaka, T., et al., European Journal of Biochemistry, 221, 889–897 (1994).

Electroporation Protocol of BTX® Electronic Genetics titled Electro Cell Manipulator® ECM600 Human hepatocelluar carcinoma Hep G2 (1991).

Mestre, J. R., et al., Cancer Research 57 (Mar. 15, 1997).

* cited by examiner

Primary Examiner—Carla J. Myers

(57) ABSTRACT

Cells are transfected with a construct containing transcriptional promoter element(s) that have been implicated in carcinogenesis or inflammation ligated to a reporter gene. Determination of inhibition of activation of said promoter element(s) by putative agent indicates the agent is a candidate as a drug or source of a drug for prophylaxis or treatment of cancer or inflammation. The method has particular application to screening agents as candidates for drugs or sources of drugs for prophylaxis or treatment of human disorders caused or mediated by cyclooxygenase-2 and/or matrix metalloproteinases.

2 Claims, 6 Drawing Sheets

US 6,200,760 B1

METHOD OF SCREENING AGENTS AS CANDIDATES FOR DRUGS OR SOURCES OF DRUGS

CROSS-REFERENCE TO RELATED APPLICATIONS

This application is the national phase of PCT/US98100023, filed Jan. 12, 1998, which claims the benefit of U.S. Provisional Application No. 60/038,254, filed Feb. 24, 1997.

This invention was made at least in part with Government support under grant CA68136 from the National Cancer Institute. Therefore, the Government has certain rights in the invention.

TECHNICAL FIELD

This invention is directed to a method of screening agents for potential as drugs or sources of drugs, and especially for screening agents for potential as drugs for disorders caused or mediated by the expression of genes involved in inflammation and/or carcinogenesis.

BACKGROUND OF THE INVENTION

There is strong evidence that cyclooxygenase-2 (COX-2) is important in carcinogenesis and that inhibition of COX-2 protects against tumor formation. Moreover, COX-2 is known to be associated with inflammatory responses incident to a number of disorders, and major pharmaceutical companies are actively involved in the development of selective COX-2 inhibitors to treat inflammation.

There is also strong evidence that matrix metalloproteinases are associated with carcinogenesis and inflammation and are involved in tumor metastasis. The term "matrix metalloproteinase" is referred to hereinafter as "MMP".

One of the limitations of drug discovery is the time and expense involved in identifying candidate compounds. There is, at present, no rapid and easy method for identifying sources of novel anti-cancer compounds and/or anti-inflammatory compounds.

SUMMARY OF THE INVENTION

It has been discovered herein that determining whether an agent suppresses the stimulation of a gene promoter that has been implicated in carcinogenesis, or inflammation, is an effective tool for screening agents as candidates for preventing or treating cancer and/or inflammation.

The invention herein relying on this discovery, is directed at a method for screening agents as candidates for prophylaxis or treatment of cancer or inflammation. The method relies on cells that are transfected with a construct containing transcriptional promoter element(s) that have been implicated in carcinogenesis or inflammation ligated to a reporter gene. Determination in the method, of inhibition of activation of said transcriptional promoter element(s) by agent which is being screened, indicates the agent is a candidate as a drug or source of a drug for prophylaxis or treatment of cancer or inflammation. Thus, a method herein is directed to screening agents as candidates for prophylaxis or treatment of cancer or inflammation and comprises (a) providing cells that are transfected with a construct containing transcriptional promoter element(s) that have been implicated in carcinogenesis or inflammation ligated to a reporter gene, and (b) determining whether putative agent inhibits activation of said transcriptional promoter element (s) with a determination of inhibition indicating that the putative agent is a candidate as a drug or as a source of a drug for prophylaxis or treatment of cancer or inflammation. The method has particular application to screening agents as candidates for drugs for prophylaxis or treatment of mammalian (e.g., human) disorders caused or mediated by cyclooxygenase-2. In this case, putative therapeutic agents are investigated for their ability to suppress stimulation of cyclooxygenase-2 promoter activity by exogenous stimulus. The method also has particular application to screening agents as candidates for drugs for prophylaxis or treatment of mammalian (e.g., human) disorders caused or medicated by MMPs. In this case, putative therapeutic agents are investigated for their ability to suppress stimulation of MMP promoter activity by exogenous stimulus.

There are a plurality of transcriptional promoter elements in cyclooxygenase-2 and in other genes, e.g., the Phorbol Ester Responsive Element (TRE), Nuclear Factor-κB(NF-κB) and a cyclic AMP response element (CRE), that have been implicated in carcinogenesis and in inflammatory response. In one embodiment of the invention herein, a battery of screenings are carried out on a putative agent utilizing in each case cells transfected with a different construct and/or transfected cells activated with a different activator. In the method of this embodiment, both specificity or sensitivity (where the putative agent inhibits one or less than all the transcriptional promoter elements) and breadth of activity are determined. The more different transcriptional promoter elements a putative agent inhibits and the more different activators a putative agent suppresses, the greater the likelihood is that the agent is an effective drug or the source of an effective drug for the prevention or treatment of cancer and/or inflammation. This embodiment increases the predictive value of the method herein.

As used herein, the term "transcriptional promoter element(s) that have been implicated in carcinogenesis or inflammation" means element(s) that mediate the transactivation function of transcription factors that control expression of the COX-2 gene or members of the MMP gene family.

As used herein the term "MMP gene family" and "MMP" includes genes that express collagenase(s), genes that express gelatinase(s), genes that express elastin, genes that express stromelysins, and other genes that express matrix metalloproteinases.

DETAILED DESCRIPTION

Figure 1A:
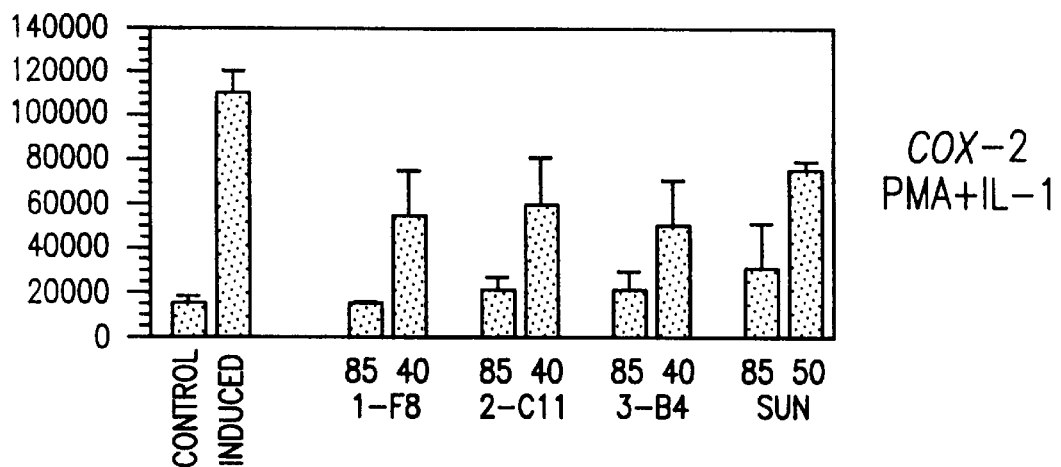
FIGS. 1a–1f each depict bar graphs showing inhibition results in terms of light units from luciferase activity where different construct/activator combinations are used in testing on four plant extracts as described in Example II.

We turn now to the method herein for screening agents as candidates for drugs for prophylaxis or treatment of mammalian disorders caused or mediated by cyclooxygenase-2 expression. Cells transfected with a construct comprising a 5'-flanking region of the human cyclooxygenase-2 gene or equivalent thereof, e.g., synthetic equivalent therefor, or other transcriptional promoter element of the human cyclooxygenase-2 gene ligated to a reporter gene are treated with an activator of cyclooxygenase-2 promoter activity. The agent being screened is tested for its ability to suppress stimulation of the cyclooxygenase-2 promoter. The agent is a candidate as a drug or source of a drug for prophylaxis or treatment of mammalian disorders caused or mediated by cyclooxygenase-2 expression if stimulated promoter activity is reduced by the agent.

We turn now to the method herein for screening agents as candidates for drugs for prophylaxis or treatment of mammalian disorders caused or mediated by MMP expression. Cells transfected with a construct containing a transcriptional promoter element from the human stromelysin gene or equivalent thereof, e.g., synthetic equivalent thereof, of from other MMP gene, or equivalent thereof, e.g., synthetic equivalent thereof, ligated to a reporter gene are treated respectively with an activator of stromelysin or other MMP promoter activity. The agent being screened is tested for its ability to suppress stimulation of the promoter. The agent is a candidate as a drug or source of a drug for prophylaxis or treatment of mammalian disorders caused or mediated by MMP expression if stimulated promoter activity is reduced by the agent.

Where an agent is determined to inhibit stimulation of both cyclooxygenase-2 promoter and also MMP promoter, this indicates a higher likelihood of anticancer or antiinflammatory property than inhibition in only one of the cases.

We turn now to the transcriptional elements of the constructs.

The sequence of the human cyclooxygenase-2 gene is described in Kosaka, T., et al., Eur. J. Biochem. 221, 889–897 (1994) which is incorporated herein by reference.

The region of human cyclooxygenase-2 gene constituting said 5'-flanking region may contain, for example, 1475 bases 5' of the cyclooxygenase-2 transcription start site having, for example, the sequence −1475/+59, or 1432 bases 5' of the cyclooxygenase-2 transcription start site having, for example, the sequence −1432/+59 or 375 bases 5' of the cyclooxygenase-2 transcription start site having, for example, the sequence −375/+59, or 327 bases 5' of the cyclooxygenase-2 transcription start site having, for example, the sequence −327/+59. Other transcriptional promoter elements of the cyclooxygenase-2 gene, for use herein, for forming said construct include, for example, the cyclic AMP response element (−59/−53), the NF-κB element (−223/−214), and the NFIL-6 element (−132/−124). Synthetic promoter elements such as synthetic NF-κB may be used in place of a promoter element from the cyclooxygenase gene, for example, the NF-κB motif from HIV/IgK which is described in Chang, C. C., et al., Oncogene 9(3), 923–933 (1994) which is incorporated herein by reference. The specific sequence actually used for NF-κB in Example II hereinafter is that set forth in Table 1 of Chang et al. for the mu IgK gene but the sequence set forth for NF-κB in said Table 1 for the HIV gene is equivalent. The term "HIV/IgK" is used herein in relation to NF-κB as indicating the equivalence of the NF-κB sequences for mu IgK and HIV.

The sequence of the human stromelysin gene is described in Quinones, S., et al., J. Biol. Chem. 264 (14), 8339–8344 (1989) which is incorporated herein by reference. The transcriptional promoter elements thereof are known and include the region −1303 to −11 relative to the transcription start site. A synthetic transcriptional promoter element for the human stromelysin gene is denoted herein as Ets2/AP-1 and consists of one copy of an inverted repeat of an Ets motif found in the stromelysin promoter which binds the Ets2 homodimer (described in Yang, B.-S., et al., Molecular and Cellular Biology, February 1996, pages 538–547 which is incorporated here by reference) and two synthetic copies of an AP-1 binding motif (having the sequence TGAGTCA) which is positioned 3' to the Ets sites. The AP1 site sequence from the stromelysin promoter is given in Buttice, G., et al., Nucleic Acids Research, Vol. 19, No. 13, 3723–3731 (1991) which is incorporated herein by reference. The synthetic transcriptional promoter element based on the NF-κB motif described above in conjunction with the COX-2 gene is also a synthetic transcriptional promoter element for some MMP genes.

The preferred reporter gene to which a promoter element is ligated is luciferase as described in Inoue, H., et al., FEBS Lett., 350, 51–54 (1994). Other reporter genes for use for this purpose include, for example, β-galactosidase gene (βgal) and chloramphenicol acetyltransferase gene (CAT) Assays for expression produced in conjunction with each of these reporter gene elements are well-known to those skilled in the art. An assay in connection with the luciferase gene and an assay in connection with the βgal gene are described in Example I hereinafter.

Constructs are prepared by ligating transcriptional promoter elements to the reporter genes by methods well-known in the art, e.g., by utilizing restriction enzymes to cut the reporter gene in appropriate portion to provide binding sites for the transcriptional promoter elements, incubating the restriction enzyme treated reporter gene with the transcriptional promoter elements and screening for the recombinants. Formation of construct of COX-2 transcription start site (−1432/+59) ligated to luciferase gene is described in Inoue, H., et al., FEBS Lett., 350, 50–54 (1994) which is incorporated herein by reference.

Cell lines for transfection to provide cells transfected with construct for use herein include cells involved in carcinogenesis or inflammation. Examples of cell lines for transfection to provide cells transfected with construct for use in the method herein include, for example, 1483 squamous carcinoma cells as described in Sacks, P. G., et al., Cancer Res. 48, 2858–2866 (1988) which is incorporated herein by reference; and human chondrocyte cell line SW1353 having accession No. ATCC HTB 94 and available from the American Type Culture Collection, 12301 Parklawn Drive, Rockville, Md. 20852.

Either transient systems or stably transfected cell lines can be used.

Transfection to provide a transient system can be carried out using pFx-3 as described in Example I hereinafter. In this case, standardization can be obtained by co-transfecting a plasmid which expresses β-galactosidase, e.g., pCMV.SPORTβgal, as described in Example I hereinafter. Thus, when cyclooxygenase-2-luciferase and pCMV.SPORTβgal are co-transfected, the luciferase values obtained in the assay can be normalized using β-galactosidase activity.

A preferred method of transfection to provide a transient system involves utilizing electroporation, very preferably square wave electroporation. The electroporation causes temporary openings in the cells whereby the construct can enter inside the cell. This method can be carried out in any cell culture medium and very preferably is carried out in DME/F12 cell culture medium. As used herein, the term "DME/F12" means a 1:1 mixture of Dulbecco's Modified Eagle's Medium and Ham's Nutrient Mixture F12. The DME/F12 medium is available as product #56498 from JRH Biosciences of Lenexa, Kans. The contents of the medium is set forth on page 39 of Catalog #0195 of JRH Biosciences, which is incorporated herein by reference. Very preferably the cell culture medium is supplemented with from 2 to 10% by volume of fetal bovine serum; the fetal bovine serum causes increase in survivability of cells subjected to electroporation in the transfection method, so a lower cell density can be used during electroporation to obtain the same result compared to when the fetal bovine serum is not present. In a preferred electroporation method, there are employed 500 µl transfection medium, from $6 \times 10^6$ to $20 \times 10^6$ cells and 25 µg of construct. A convenient electroporation time is 70 milliseconds. The voltage used will vary, e.g., from 110 volts to 200 volts, depending on the cell line and construct. A preferred voltage for a particular cell line and construct may be determined by preparing a plurality of cuvettes with the same amount of cells and DNA and utilizing a different voltage for each cuvette, e.g., 100 volts for one cuvette, 120 volts for another cuvette, 130 volts for another cuvette, etc., and subsequently using that voltage for the same cells and construct that is determined to provide the best yield. In a very preferred method, a single electroporation is utilized to transfect cells which are subsequently diluted with additional cell culture medium to a volume such as to provide aliquots thereof of the same composition for a plurality of wells, e.g., 96 wells, for use for determinations, to provide a high throughput system and standardization without the need to use a standardizing plasmid.

For transient systems, the results need to be compared to what occurs when the method is carried out in the absence of putative agent.

Transfection to provide a stable system, i.e., a stably transfected cell line, is obtained by standard methods.

It is preferred to compare results with those obtained for agent of known effect, for example, all-trans retinoic acid which is tested in Example I below.

The activator can be any substance which is known to stimulate transcription. Such activators include, for example, tumor promoters such as phorbol esters (e.g., phorbol myristate acetate, e.g., phorbol 12-myristate 13-acetate), serum (e.g., fetal bovine serum), cytokines (e.g., tumor necrosis factor or interleukin-1), growth factors (e.g., epidermal growth factor which may be referred to as EGF), benzo[a]pyrene, lipopolysaccharide, bile acids (e.g., chenodeoxycholate and deoxycholate), free radical producing compounds such as hydrogen peroxide and cyclic AMP generating agents such as forskolin. The particular activators utilized will depend on the transcriptional promoter element in the construct. For the broad and medium cyclooxygenase-2 promoter regions (−1475/+59, −1432/+59, −375/+59, and −327/+59), phorbol esters and epidermal growth factor are useful as activators. For cyclic AMP response elements, cyclic AMP generating agents are useful as activators. For NF-κB elements, free radical producing agents, phorbol esters and cytokines are useful activators. For the Ets2AP-1 promoter, phorbol esters are useful as activators.

The agent to be screened is one whose therapeutic properties are unknown for the use being screened for and can be, for example, extracts from natural products such as plant or marine organisms, compounds purified from natural products, and synthetic compounds. Automating the method herein allows large numbers of potential medicinal agents to be screened by the method herein.

All-trans retinoic acid suppresses phorbol ester induction of cyclooxygenase-2 gene promoter activity in 1483 squamous carcinoma cells. This result is obtained when transient transfections are performed using a human COX-2 promoter construct containing 1432 bases of 5'-flanking region DNA ligated to luciferase. This result demonstrates the feasibility of using retinoids to down-regulate phorbol ester mediated induction of cyclooxygenase-2 by suppressing transcription as discussed in Mestre, J. R., et al., "Retinoids Suppress Phorbol Ester-Mediated Induction of Cyclooxygenase-2", Cancer Res. 57, 1081–1085 (1997) which is incorporated herein by reference.

In the method herein, the transfected cells are preferably treated with agent being screened prior to being exposed to the activator, i.e., pretreatment. Good results are also obtained when the activator and agent being screened are given simultaneously.

We turn now to the embodiment of the invention where a battery of screenings are carried out on a putative agent utilizing in each case cells transfected with a different construct and/or transfected cells activated with a different activator. For example, the constructs can be TRE-luciferase and NF-κB-luciferase activated respectively by phorbol ester and lipopolysaccharide. Inhibition by putative anticancer or antiinflammatory agent of activation in each case would be determined. Inhibition in all cases indicates higher likelihood of anticancer or antiinflammatory property than inhibition in a single case.

In a very preferred method herein for screening for candidates for treatment of an inflammatory and/or carcinogenic disorder, the cells that are transfected are chondrocytes and a battery of screenings are carried out on each putative compound, where in one case the chondrocytes are transfected with a construct containing the COX-2 promoter and the activator is phorbol myristate acetate used in combination with interleukin-1; in another case, the chondrocytes are transfected with Ets2/AP-1 transcription promoter elements and the activator used is phorbol myristate acetate; in another case, the chondrocytes are transfected with construct containing NF-κB transcription promoter element (a synthetic element containing the NF-κB motif from HIV/IgK) and the activator is interleukin-1; in another case, the chondrocytes are transfected with construct containing said NF-κB transcription promoter element and the activator is tumor necrosis factor-alpha; and in another case, the chondrocytes are transfected with construct containing said NF-κB transcription promoter element and the activator is phorbol myristate acetate. The more cases of inhibition of activation, the higher the likelihood of antiinflammatory and therefore anticancer property.

It is preferred to include as a control, a determination for putative agent on the same cell type as is transfected with construct for testing for inhibition of activation but instead transfected with construct containing Sp1 and reporter gene where activation is carried out using the same activator of transcriptional promoter element as is used in testing in the experimental runs (i.e., not control runs). Sp1 has not been implicated in carcinogenesis or inflammation, and there is not much change in activity when Sp1-containing construct is treated with activator. Thus, any reduction in activity in respect to Sp1-containing construct on treatment with putative agent and inducer will be caused by agents that inhibit reporter (e.g., luciferase) activity or by toxicity of the putative agent and not by inhibiting of transcription factor so that ostensible inhibition of construct containing transcription promoter element implicated in carcinogenesis or inflammation by the same putative agent as causes reduction in activity in respect to Sp1-containing construct, will be shown to be caused by reporter inhibiting activity or by toxicity of the putative agent and not by inhibition of activation by the putative agent. An example of this where the reporter gene is luciferase follows. In a first case, any reduction of luciferase activity of activated construct in cells transfected with construct containing transcriptional promoter element(s) that have been implicated in carcinogenesis or inflammation, treated with putative agent, is determined compared to luciferase activity of activated construct in cells transfected with construct containing transcriptional promoter element(s) that have been implicated in carcinogenesis or inflammation that have not been treated with the putative agent. In a second case, other cells from the same cell line that provides cells for transfection for said construct are transfected with Sp1 luciferase, and the transfected cells are treated with the putative agent, to determine the extent to which said agent causes reduction in luciferase activity. The result in the second case shows the extent to which reduction in luciferase activity determined for construct containing transcriptional promoter element(s) that have been implicated in carcinogenesis or inflammation is not due to inhibition of activation of transcriptional promoter element(s) by putative agent but rather is due to luciferase activity inhibition or toxicity of the putative agent. Sp1 luciferase construct is commercially available from Promega under the name pGL3 Promoter. The Sp1 sequences in this construct are derived from a portion of the SV40 early region promoter as contained in the $pA_{10}CAT$ construct described in Laimons, L., et al., Proc. Natl. Acad. Sci. U.S.A., 79, 6453–6457 (1982), which is incorporated herein by reference.

The invention is illustrated by the following examples:

EXAMPLE I

Screening for Drugs which Suppress Induction of COX-2

A COX-2 promoter construct was prepared containing 1432 bases 5' of the COX-2 transcription start site (−1432/+59) ligated to luciferase gene. The plasmid is described in Inoue, H., et al., FEBS Lett., 350, 51–54 (1994). The plasmid is referred to hereinafter as "COX-2 promoter construct."

1483 squamous carcinoma cells (described in Sacks, P. G., et al., Cancer Research, 48, 2858–2866 (1988)) were seeded at a density of $8 \times 10^5$ cells/well in six well dishes and grown to 30–40% confluence in DMEM/F-12 containing 10% fetal bovine serum (FBS). For each well, 1.8 μg of COX-2 promoter construct and 0.2 μg pCMV.SPORTβgal (from Life Technologies, Inc. of Grand Island, N.Y.) were co-transfected into the 1483 cells using pFx-3 at a 1:12 ratio of DNA to lipid according to the manufacturer's (Invitrogen, San Diego, Calif.) instructions. After transfection, cells were treated with DMEM/F-12 containing agent being tested (in this case, all-trans-retinoic acid, also referred to herein as ATRA) at a concentration of 1 μM or vehicle (0.01% DMSO). Twenty-four hours later, the medium was replaced with DMEM/F-12 with or without phorbol 12-myristate 13-acetate (PMA) at 50 ng/ml. The activities of luciferase and β-galactosidase were measured in cellular extract 24 hours later as follows: Each well was washed twice with PBS. Two hundred μl of 1× lysis buffer (Analytical Luminescence Laboratories, San Diego, Calif.) was added to each well for 30 minutes. Lysate was centrifuged for 5 minutes at 4 degrees C. The supernatant was used to assay the activities of luciferase and β-galactosidase. Luciferase activity was measured using a Monolight 2010 luminometer (Analytical Luminescence Laboratories) according to the manufacturer's instructions. To measure the activity of β-galactosidase, 40 μl aliquots of the supernatant were incubated with assay buffer (60 mM $Na_2HPO_4$, 1 mM $MgSO_4$, 40 mM mercaptoethanol, 10 mM KCl, and 4 mg/ml O-nitrophenyl-β-D-galactopyranoside) in a total volume of 400 μl for 30 minutes at 37 degrees C. The reaction was terminated with the addition of 500 μl of 1M $Na_2CO_3$, and the absorbance at 420 nm was determined. To adjust for differences in transfection efficiencies, the luciferase values were normalized using β-galactosidase activity. The results are depicted in FIG. 7 of Mestre, J. R., et al., Cancer Research 57, 1081–1085 (1997), which is incorporated herein by reference, wherein the columns represent the mean values and the bars represent the standard deviations. As shown in said FIG. 7, treatment with PMA induced more than a doubling in COX-2 promoter activity and all-trans-retinoic acid suppressed this effect. Comparisons between groups were made by the Students t-test. A difference between groups of P<0.05 was considered significant. The results show all-trans-retinoic acid suppressed PMA induced activation of COX-2 promoter with a difference of p=0.01. These results demonstrate the feasibility of using retinoids to inhibit phorbol ester-mediated activation of COX-2 transcription. The results suggest potential activity for retinoids as anti-cancer and anti-inflammatory agents. The results indicate the efficacy of the invention herein in screening ATRA as a candidate as an anti-cancer and anti-inflammatory drug.

In another case, the construct was the same as that used in this Example above except that the COX-2 promoter ligated to luciferase gene was −1432/+59 and the activator was epidermal growth factor (EGF). Treatment with epidermal growth factor led to approximately a 100% increase in COX 2 promoter activity in the absence of test compounds. This effect was suppressed by all-trans-retinoic acid, 13-cis-retinoic acid, retinyl acetate, and 9-cis-retinoic acid (p<0.001 compared with EGF treatment). The results are depicted in FIG. 9 of Mestre, J. R., et al., Cancer Research 57, 2890–2895 (1997), which is incorporated herein by reference. In said FIG. 9, the columns represent the mean values and the bars represent the standard deviations.

EXAMPLE II

Screening for Drugs which Suppress Induction of COX-2 or MMP

Approximately 800 natural products extracts were screened. Each was screened in a battery of screenings.

Constructs used were COX-2 promoter (−1475/+59) ligated to luciferase, Ets2/AP-1 (described above) ligated to luciferase, NF-κB ligated to luciferase and Sp1 ligated to luciferase.

The COX-2 promoter-containing construct was prepared similarly to the COX-2 promoter-containing construct used in Example I except −1475/+59 was substituted for −1432/+59.

For the Ets2/AP-1 containing construct, the Ets2/AP-1 transcriptional promoter element is that described previously and ligation to luciferase was carried out as follows: Ets2 and AP-1 synthetic DNA oligonucleotides were purchased from Integrated DNA Technologies, Inc., Coralville, Iowa. Each double stranded oligonucleotide contained a 5' BamHI site and a 3' Bgl II site relative to the top strand. The Ets2 element was inserted into the BamHI site and two copies of the AP-1 element were inserted into the Bgl II site of p1A1-LUC in the orientation described above. The luciferase reporter plasmid 1A1-LUC was constructed by inserting a synthetic minimal rat CYP1A1 promoter (bases −1 through −44) 5' to the luciferase gene in a modified version of the pGL3-Basic Vector (purchased from Promega). The sequence of the rat CYP1A1 gene is found in Sogawa, K., et al., Proc. Natl. Acad. Sci. U.S.A. 81, 5066–5070 (1984) which is incorporated herein by reference.

For the NF-κB containing construct, the NF-κB transcriptional promoter element is that specifically described above from IgK, and the luciferase construct containing such promoter, pBIIXLUC, was obtained from Dr. Riccardo Dalla-Favera of the Department of Pathology, College of Physicians and Surgeons, Columbia University and is referred to in Chang, C. C., et al., oncogene 9(3), 923–933 (1994) which is cited above and is incorporated herein by reference.

Sp1 ligated to luciferase (denoted Sp1 hereinafter) for use as a control, was purchased from Promega under the tradename pGL3 Promoter.

The cell line transfected with the constructs to provide transfected cells used herein was human chondrocyte cell line SW1353 having accession No. ATCC HTB 94 and was purchased from the American Type Culture Collection.

Cells from the cell line were transiently transfected by square wave electroporation with each of the constructs as follows: Added into a tube for transfection were 500 μl DME/F12 medium supplemented with 3% by volume fetal bovine serum, $12 \times 10^6$ chondrocyte cells (SW1353) and 25 μg construct. Square wave electroporation was carried out in a 4 mm electrode cuvette using a T820 Electro Square Porator apparatus obtained from BTX/Genetronics, Inc., San Diego, Calif. Seventy milliseconds was used for the electroporation time and was selected as being a convenient time. The electroporation voltage used was 150 volts which was the voltage determined by the procedure for selecting electroporation voltage described above, to provide the best yields of transfected cells for the cell line and constructs being used. The 500 μl compositions that were subjected to electroporation were diluted into 20 ml of DME/F12 containing 10% fetal bovine serum. The 20 ml of diluted mix was plated into a 96-well plate, 200 μl per well, to give $0.12 \times 10^6$ cells per well (15–18% transfection efficiency). The contents of all the wells was essentially identical. The 96 well cell culture plates used were Cultur Plate (white) from Packard which can be counted directly in the luminometer as described below.

Twenty-four hours after transfection, except in the case of the control and in the case of runs with activator but no agent, the transfected cell compositions were treated with extract of test agent by addition of extract of test agent to wells to provide selected concentration of test agent. The admixtures for all the runs contained 0.1% dimethyl sulfoxide (DMSO). One half hour later, activator (inducer) was added to each well except for the control wells.

The following combinations of construct in transfected cells and inducer were utilized: (1) COX-2 promoter ligated to luciferase as construct and phorbol myristate acetate together with interleukin-1 as inducer; (2) Ets2/AP-1 ligated to luciferase as construct and phorbol myristate acetate as inducer; (3) NF-κB ligated to luciferase as construct and interleukin-1 as inducer; (4) NF-κB ligated to luciferase as construct and tumor necrosis factor-alpha as inducer; (5) NF-κB ligated to luciferase as construct and phorbol myristate acetate as inducer; and (6) Sp1-luciferase as construct and phorbol myristate acetate together with interleukin-1 inducer.

The phorbol myristate acetate was added to a well to provide a concentration therein of 125 nM. The interleukin-1 was added to a well to provide a concentration therein of 3 ng/ml. The tumor necrosis factor-alpha was added to a well to provide a concentration therein of 50 ng/ml.

Assay for luciferase activity was carried out 7 hours after adding inducer as follows. The contents of a well were aspirated. Directly after aspiration, there was added to a well 40 μl of a 50/50 of Packard LucLite Luciferase reagent and PBS (phosphate buffered saline) containing 1 mM $Ca^{++}$ and 1 mM $Mg^{++}$. After this, the top of each plate was covered with transparent tape and the covered plate was placed in a Packard TopCount luminometer and the results for each well in the plate were read in light units.

The results for four plant extracts where inhibition activity were determined are set forth in FIGS. 1a–1f. The four extracts for which data are shown are hexane extract of Lycopodium corneum (denoted "1-F8" hereinafter and in FIGS. 1a–1f), hexane/ethyl acetate extract of Selaginella stellate (denoted "2-C11" hereinafter and in FIGS. 1a–1f), hexane/ethyl acetate extract of Ambrosia peruviana (denoted "3-B4" hereinafter and in FIGS. 1a–1f), and aqueous extract of Lithospernum erythrorhizon (denoted "SUN" hereinafter and in FIGS. 1a–1f). Runs were carried out for 1-F8, 2-C11 and 3-B4 at concentrations of 85 and 40 micrograms extract on a dry weight basis (i.e., without solvents) per milliliter which are denoted respectively by "85" and "40" in FIGS. 1a–1f. Runs were carried out for SUN at concentrations of 85 and 50 micrograms per milliliter extract on a dry weight basis (i.e., without solvents) which are denoted respectively by "85" and "50" in FIGS. 1a–1f.

Figure 1B:
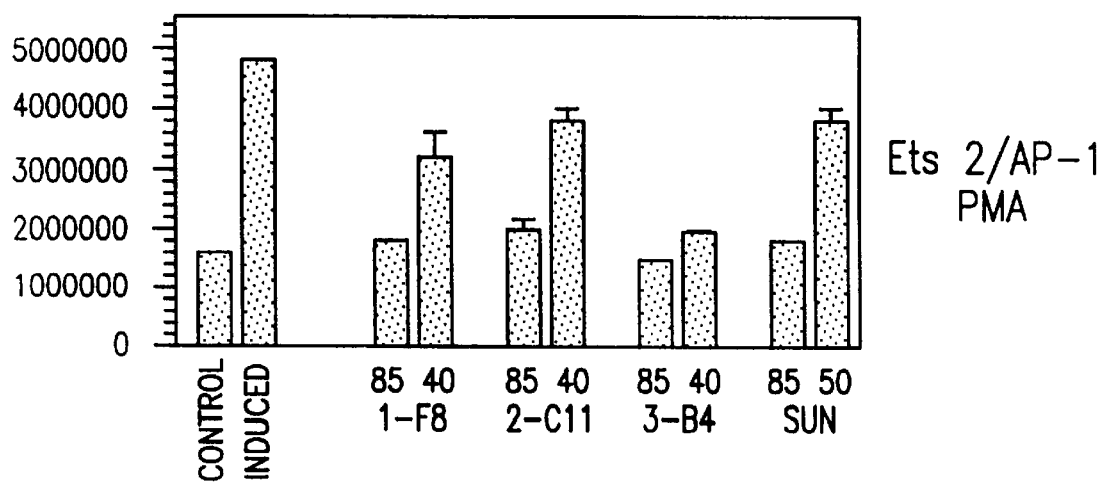
Figure 1C:
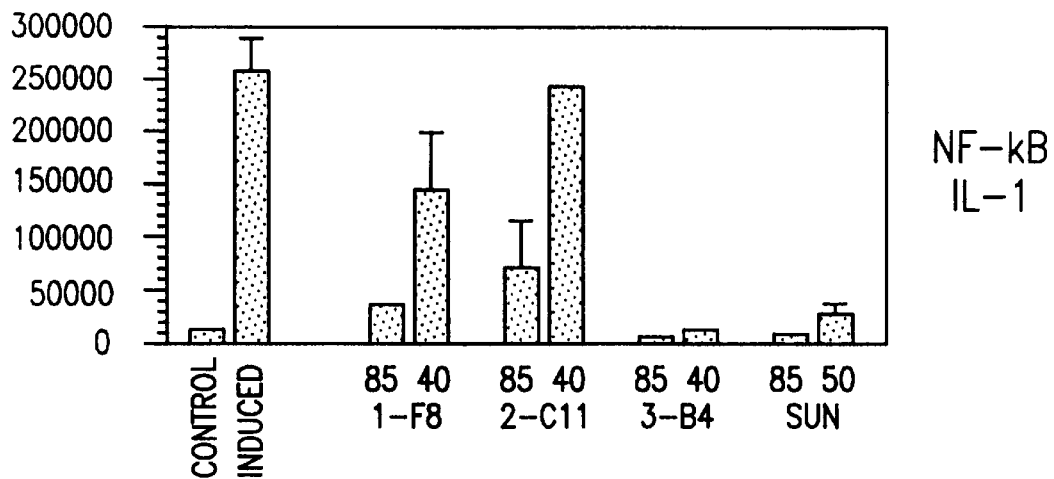
Figure 1D:
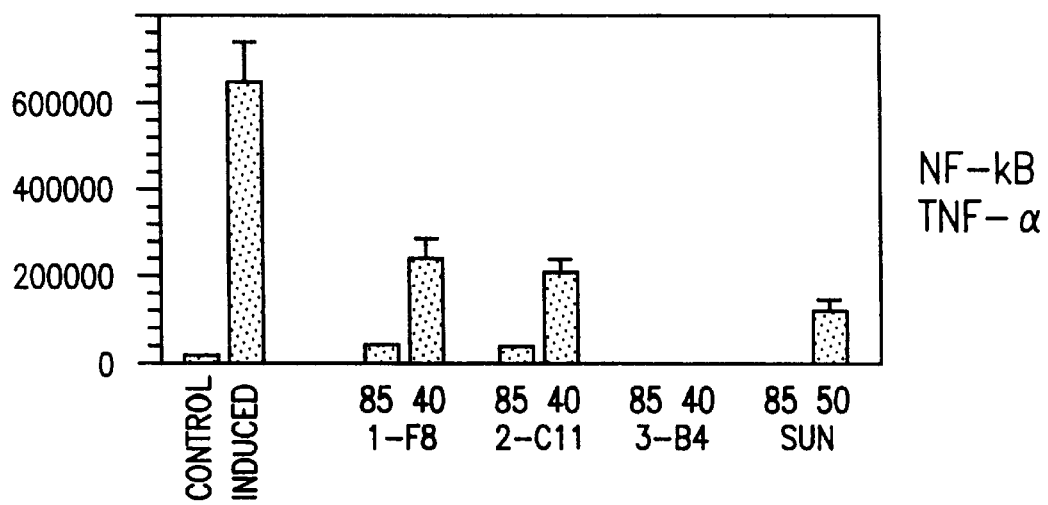
Figure 1E:
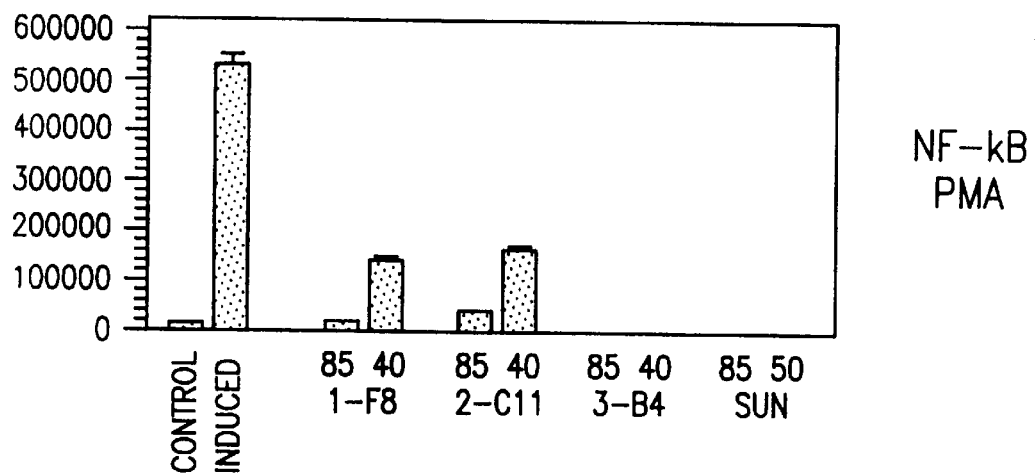
Figure 1F:
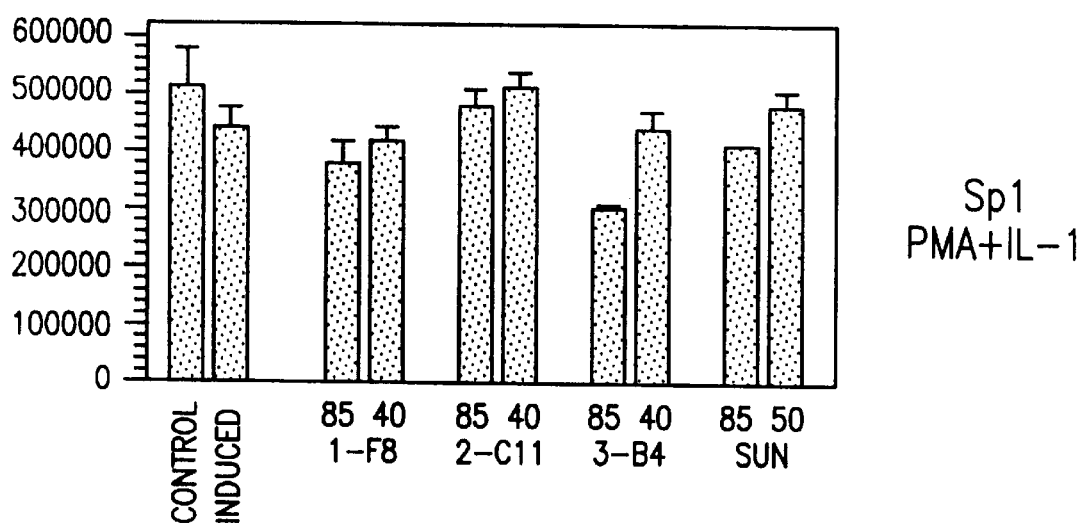
Figure 2A:
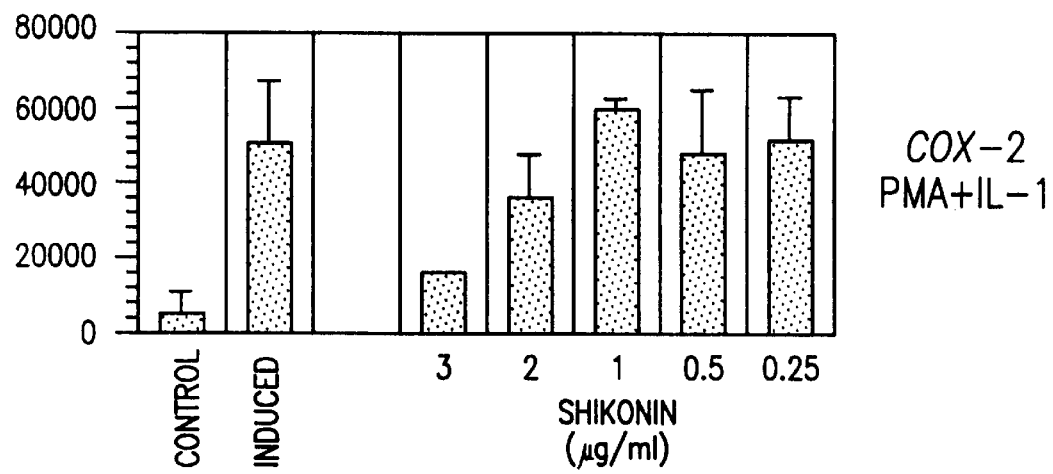
FIGS. 2a–2f each depict bar graphs showing inhibition results in terms of light units from luciferase activity where different construct/activator combinations are used in testing on shikonin as described in Example II.
Figure 2B:
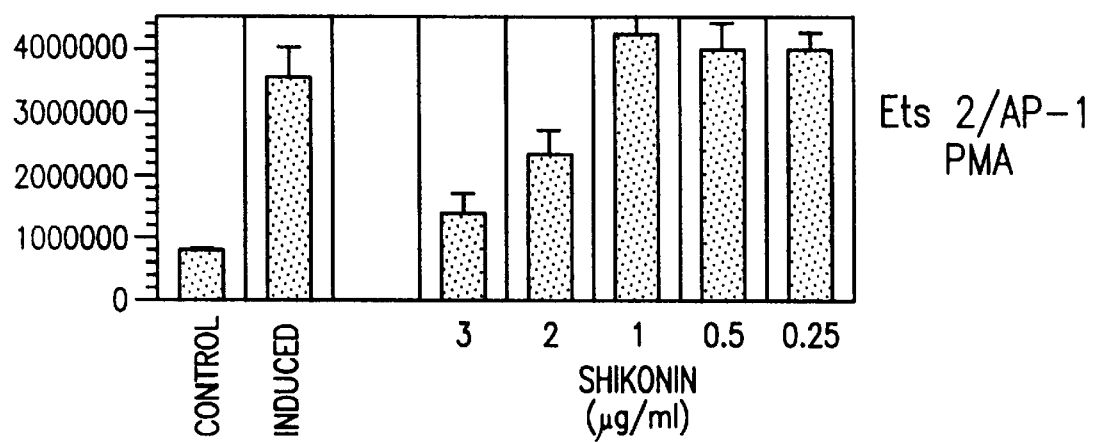
Figure 2C:
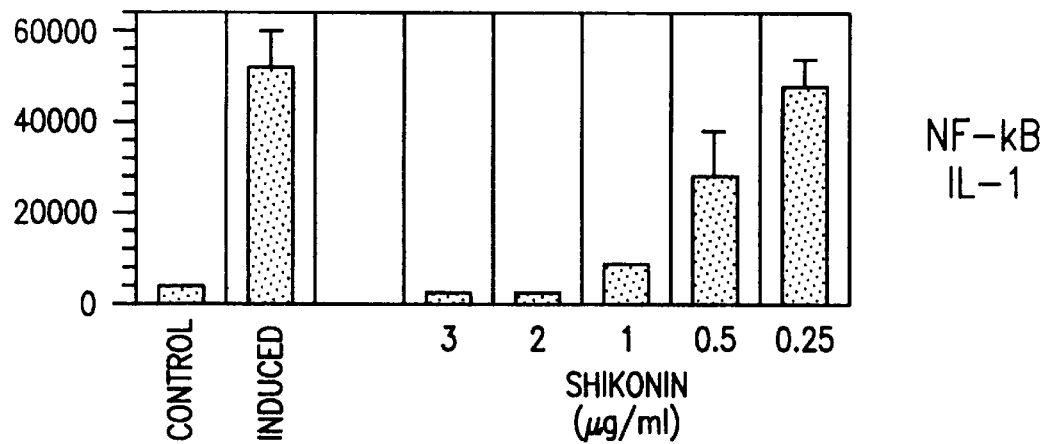
Figure 2D:
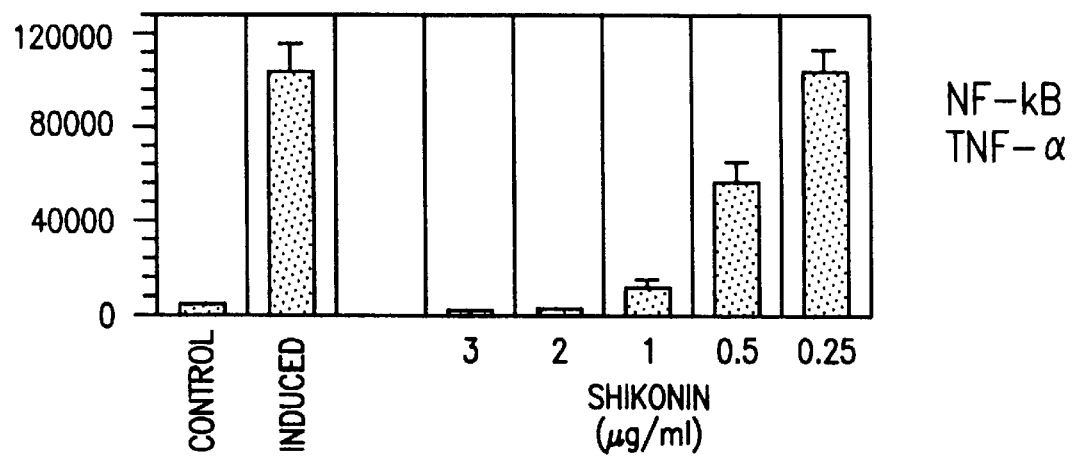
Figure 2E:
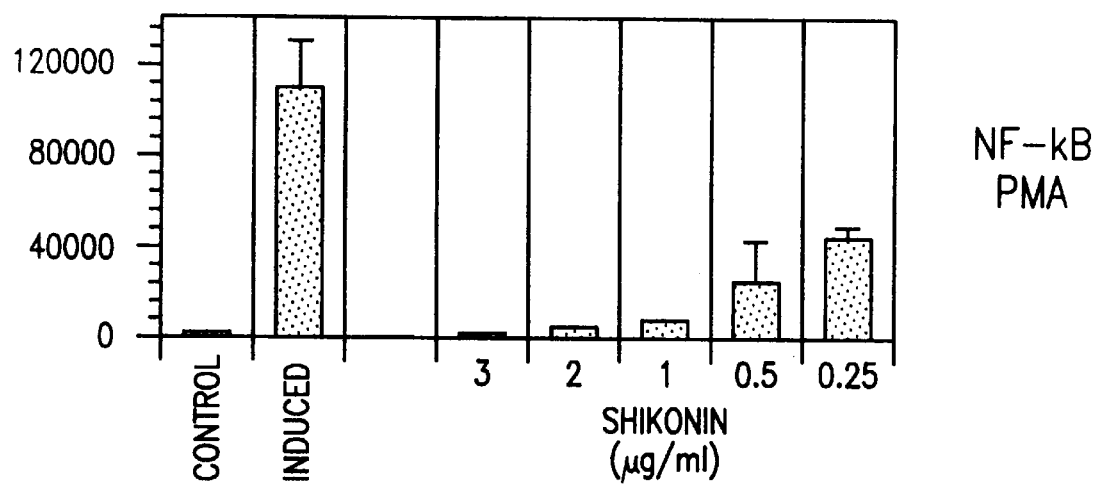
Figure 2F:
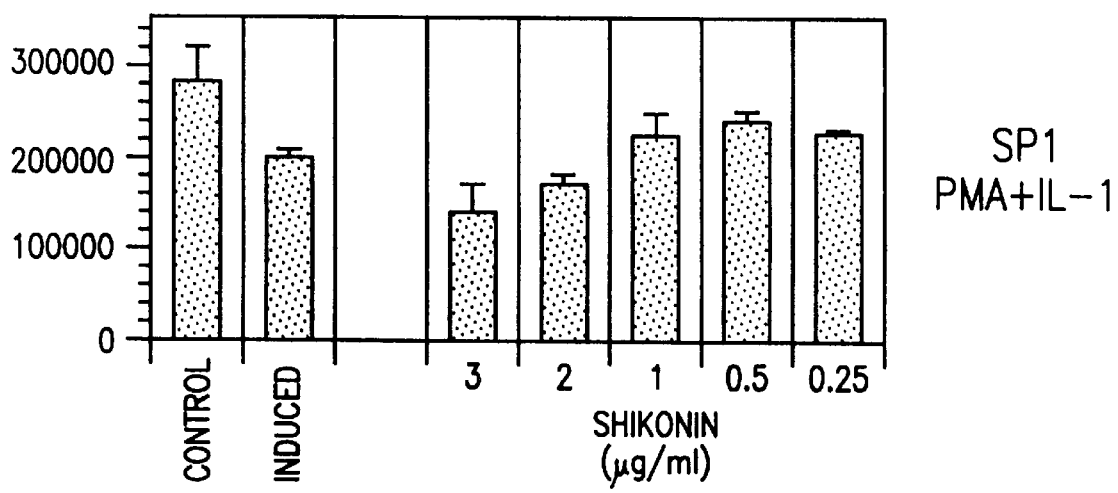

Results for combination (1) of construct in transfected cells and inducer are depicted in FIG. 1a. Results for combination (2) of construct in transfected cells and inducer are depicted in FIG. 1b. Results for combination (3) of construct in transfected cells and inducer are depicted in FIG. 1c. Results for combination (4) of construct in transfected cells and inducer are depicted in FIG. 1d. Results for combination (5) of construct in transfected cells and inducer are depicted in FIG. 1e. Results for combination (6) of construct in transfected cells and inducer are depicted in FIG. 1f.

For the runs denoted "CONTROL" in FIGS. 1a–1f, no agent or inducer was added but transfected construct was present.

For the runs denoted "INDUCED" in FIGS. 1a–1f, no agent was added but transfected construct was present and inducer was added.

The numbers along the vertical axis in each of FIGS. 1a–1f are in light units read on The Packard TopCount luminometer wherein greater numbers indicate greater luciferase activity and therefore greater transcriptional promoter activity. In FIGS. 1a–1f, the columns represent the average of duplicate values and the bars represent the range.

The results show inhibition of transcriptional activity element by 1-F8 in FIGS. 1a–1e and that a significant portion of said inhibition is not due to luciferase activity inhibition or toxicity of 1-F8 (FIG. 1f). The results show inhibition of transcriptional promoter activity by 2-C11 in FIGS. 1a–1e and that a significant portion of this inhibition is not due to luciferase activity inhibition or toxicity of 2-C11 (FIG. 1f). The results show inhibition of transcriptional promoter activity by 3-B4 in FIGS. 1a–1e and that a significant portion of this inhibition is not due to luciferase activity inhibition or toxicity of 3-B4. The results show inhibition of transcriptional promoter activity by SUN in FIGS. 1a–1e and that a significant portion of this inhibition is not due to luciferase inhibition activity or toxicity of SUN.

The results show that plant extracts 1-F8, 2-C11, 3-B4, and SUN are good candidates for treating inflammation and for preventing or treating cancer.

In another case, runs were carried out the same as above except that the test agent was shikonin, used in a concentration of 3 μg/ml, 2 μg/ml, 1 μg/ml, 0.5 μg/ml, or 0.25 μml. The results are shown in FIGS. 2a–2f where the transfected constructs and inducers were the same for FIGS. 1a and 2a, for FIGS. 1b and 2b, for FIGS. 1c and 2c, for FIGS. 1d and 2d, for FIGS. 1e and 2e, and for FIGS. 1f and 2f. Shikonin is a compound with known antiinflammatory and antineoplastic properties. The results for shikonin show that it inhibits activation of the different promoters and by different activators in a manner similar to that shown for SUN. Shikonin is present in SUN extract. The results validate the predictive power of the screen.

Variations will be evident to those skilled in the art. Therefore, the scope of the invention is intended to be defined by the claims.

What is claimed is:

1. A method for screening agents as candidates for prophylaxis or treatment of cancer or inflammation, said method comprising (a) providing cells from one cell line that are transfected with a construct containing transcriptional promoter element(s) that have been implicated in carcinogenesis or inflammation ligated to reporter gene which is luciferase, and (b) determining whether putative agent inhibits activation by activator of said transcriptional promoter element(s) wherein step (b) comprises (i) determining any reduction of luciferase activity of the construct in cells transfected with the construct treated with putative agent and activator compared to luciferase activity of the construct in cells transfected with the construct that are treated with the activator and not treated with putative agent, and (ii) determining any reduction of luciferase activity in cells from the same cell line as the cells transfected in step (a) transfected with construct in which luciferase expression is driven by Sp 1 sites treated with the putative agent and the activator compared to cells from the same cell line as transfected in step (a) transfected with construct in which luciferase expression is driven by Sp 1 sites that are treated with the activator and not treated with the putative agent, with reduction in luciferase activity in (ii) indicating inhibition of luciferase enzyme activity or toxicity by putative agent and indicating the extent to which reduction in luciferase activity determined in (i) is due to inhibition of luciferase enzyme activity or toxicity by putative agent, with a determination of inhibition in step (b) being demonstrated by reduction of luciferase activity in step (i) not due to inhibition of luciferase enzyme activity or toxicity by putative agent as determined in step (ii) and indicating that the putative agent is a candidate as a drug or a source of a drug for prophylaxis or treatment of cancer or inflammation.

2. A method of screening agents as inhibitors of COX-2 expression, said method comprising (a) providing cells that are transfected with constructs containing the COX-2 promoter or elements from the COX-2 promoter ligated to a reporter gene, and (b) determining whether a putative agent inhibits activation of said promoter or elements with a determination of inhibition indicating that the putative agent is a candidate as a drug or as a source of a drug for inhibition of COX-2 expression, wherein a battery of screenings is carried out on a putative agent, and for that battery of screenings, step (a) comprises providing cells that are transfected with a COX-2 promoter containing construct, cells that are transfected with an AP-1 element containing construct and cells that are transfected with a NF-κB element containing construct and step (b) comprises determining whether the putative agent inhibits activation of the COX-2 promoter, AP-1 element and NF-κB element containing constructs wherein inhibition of activation of one or more of said promoter or said elements is correlated with likelihood of an agent being an inhibitor of COX-2 expression.

\* \* \* \* \*